United States Patent [19]
Gadsby et al.

[11] Patent Number: 5,309,909
[45] Date of Patent: May 10, 1994

[54] COMBINED SKIN PREPARATION AND MONITORING ELECTRODE

[75] Inventors: Peter D. Gadsby, Duvall; Robert A. Niskanen; David S. Paeth, both of Seattle, all of Wash.

[73] Assignee: Physio-Control Corporation, Redmond, Wash.

[21] Appl. No.: 888,041

[22] Filed: May 22, 1992

[51] Int. Cl.⁵ .................................................. A61B 5/0408
[52] U.S. Cl. .................................... 128/639; 128/640; 128/641
[58] Field of Search ....................... 128/639–641, 128/643, 644, 758, 802, 803; 607/149, 152, 153

[56] References Cited

U.S. PATENT DOCUMENTS

| Re. 25,637 | 9/1964 | Kravitz et al. | 128/253 |
|---|---|---|---|
| 1,699,012 | 11/1927 | Naylor . | |
| 2,009,562 | 12/1933 | Okumura | 128/333 |
| 3,505,993 | 12/1965 | Lewes et al. | 128/2.06 |
| 3,774,592 | 11/1973 | Lahr | 128/2.1 |
| 4,004,578 | 1/1977 | Palmius | 128/2.06 |
| 4,126,126 | 11/1978 | Bare et al. | 128/639 |
| 4,311,152 | 1/1982 | Modes et al. | 128/641 |
| 4,473,083 | 9/1984 | Maganias | 128/743 |
| 4,526,176 | 7/1985 | Bremer et al. | 128/641 |
| 4,685,466 | 8/1987 | Rau | 128/639 |
| 4,920,968 | 5/1990 | Takese | 128/639 |
| 4,995,392 | 2/1991 | Sherwin et al. | 128/639 |

FOREIGN PATENT DOCUMENTS 2643130  6/1978  Fed. Rep. of Germany ...... 128/639

*Primary Examiner*—Lee S. Cohen
*Attorney, Agent, or Firm*—Christensen, O'Connor, Johnson & Kindness

[57] ABSTRACT

Disclosed is a combined skin preparation and monitoring electrode (12). The electrode reduces motion artifacts in recording biopotentials by penetrating a patient's skin prior to acquiring biopotentials. Penetration of the skin reduces skin impedance and the skin's propensity to generate motion artifacts. The electrode has a resilient dome (16) with penetration tines (18) extending from the concave inner surface of the dome. Upon application of a force to the dome, the dome moves from a first position to a second position, forcing the penetration tines into a patient's skin. Upon removal of the force, the dome moves back to its original configuration, withdrawing the penetration tines from the patient's skin.

20 Claims, 6 Drawing Sheets

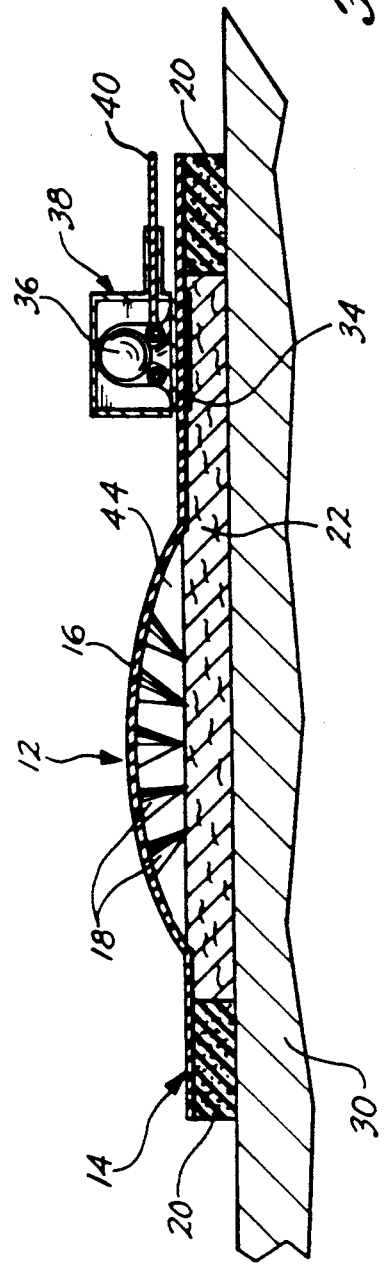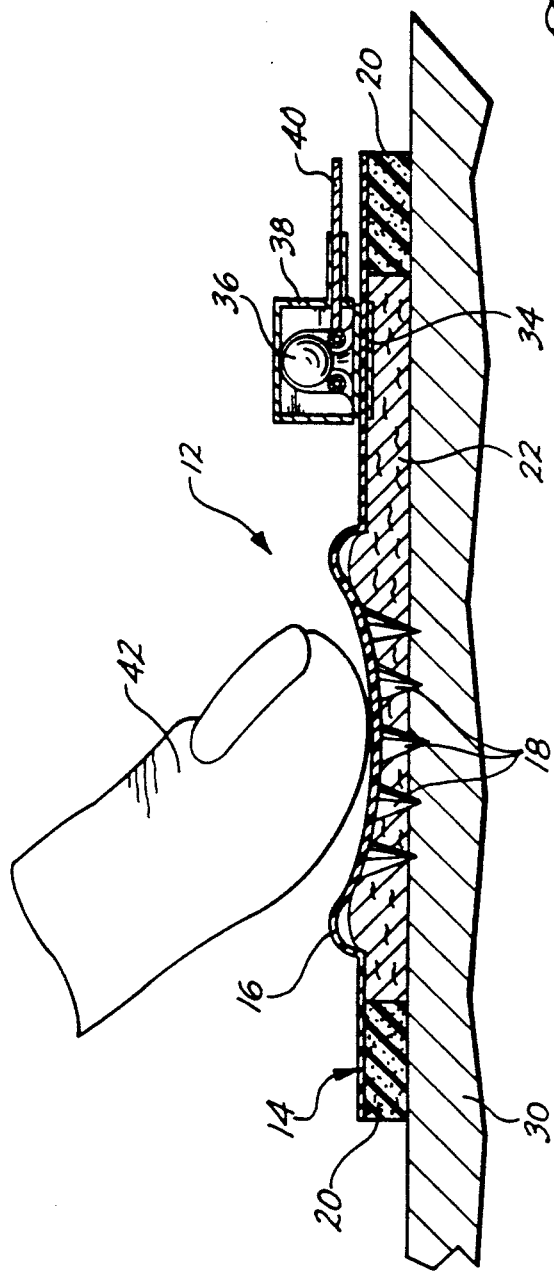

COMBINED SKIN PREPARATION AND MONITORING ELECTRODE

FIELD OF THE INVENTION

This invention relates to medical electrodes which are applied to a patient's skin prior to monitoring biopotentials, and in particular, to electrodes that penetrate the outermost layer of the skin to reduce the patient's skin impedance and the skin's potential to generate varying voltages.

BACKGROUND OF THE INVENTION

Diagnosis and treatment of many medical illnesses require monitoring and recording biopotentials of a patient. Biopotentials are voltages generated between points in living tissue. An example of a biopotential is the electrical activity of the heart that is typically recorded in the form of an electrocardiogram (ECG). The electrical activity of the heart is associated with both ion movement and ion concentration, as opposed to electron movement. Skin-mounted monitoring electrodes are used to transduce the ion movement into electron movement to be displayed as voltage or a time-dependent function of voltage called a signal. The signal is a composite of several potentials, in addition to those generated by the heart. These potentials include the half-cell potential of the electrode and the potential created by the ion concentration gradient developed across the skin, referred to as the skin potential.

It is well known in the medical field that there are a number of problems associated with monitoring biopotentials through the use of skin-mounted monitoring electrodes. One such problem is related to an unwanted signal that is created by skin motion under the electrodes. Skin has a complex electrical impedance that is inhomogeneous over the extent of the skin surface. The skin is composed of two principal layers; namely, the epidermis and the dermis. The epidermis includes the stratum corneum or horny layer as the outermost layer of skin, the stratum granulosum which is adjacent the stratum corneum, and the stratum germinativum or innermost layer of the epidermis. The stratum corneum is composed of keratin containing dead cells that have lost their nuclei. These cells are approximately 0.5 to 0.8 micrometers ($\mu$m) thick and about 3 $\mu$m in diameter. The stratum corneum varies in thickness from approximately 15 cell layers thick on the abdomen, 45 layers thick on the arms, to upwards of several hundred layers thick on the palms and soles. An additional stratum lucidum layer is found in the skin of the palm (hand) and sole (foot) and lies directly beneath the stratum corneum. The dermis is composed of loose connective tissue which contains numerous capillaries, lymphatics, nerve endings, hair follicles, sebaceous glands, sweat glands, and smooth muscle fibers.

The major contributor to skin impedance is associated with the stratum corneum. When the skin is deformed by either compression or extension, a variation in both the skin impedance and the potential between the inside and outside layers of the skin occurs. This variation in skin potential is referred to as a motion artifact or wandering baseline and cannot be easily separated from the biopotential signal of interest. If the motion artifact is severe enough it can mask or hinder the correct diagnosis of the patient's condition. Motion artifact problems are commonly associated with patient's undergoing stress testing, ambulation, or emergency transport whereby motion of the patient causes disturbance of the skin underneath the electrodes.

It is commonly known among medical practitioners that light abrasion or penetration of a patient's skin reduces skin impedance and thereby reduces the effect of skin motion. Methods of skin abrasion have included the use of sandpaper, SCOTCH-BRITE TM abrasive pads, blood lancets, gels containing abrasives, brisk rubs with gauze pads or brushes, and even dental burrs. Methods of skin preparation vary among practitioners; however, the effectiveness of each procedure depends upon the skill of the practitioner and time available. If the skin preparation that was performed is inadequate, the electrode has to be removed, the skin site has to be reprepped, and a new electrode has to be reattached.

Various electrode systems have automated skin electrode application and skin preparation, including an abrading disc and motorized applicator gun as disclosed in Modes et al., U.S. Pat. No. 4,311,152. However, the electrode and applicator gun are complex, relatively expensive and not without some skin trauma in use. Other art has suggested piercing the skin as a method of skin preparation, for example, Lahr, U.S. Pat. No. 3,774,592, and Lewes et al., U.S. Pat. No. 3,505,993. Lahr employs a specialized electrode that includes an absorbent pad saturated with a conductive material. The electrode is adhesively affixed to the skin. The bristles of a separate brush are applied to the back of the electrode and forced through the saturated absorbent pad and into the skin. This method generally results in reliable contact with the skin; however, the method requires a practitioner to perform a number of steps and does not limit the penetration depth of the bristles into the skin. Lewes et al. disclose an electrode that also pierces the skin using rigid metal projections which penetrate into the epidermis. A disadvantage of the electrode disclosed in Lewes et al. is that the projections remain in the skin during the measurement, which could result in undue laceration of the skin should the electrode move with respect to the skin and also contribute spuriously to the electrode half-cell potential.

SUMMARY OF THE INVENTION

The invention is directed toward an electrode that performs skin preparation prior to receiving biopotentials. The electrode prepares the patient's skin by substantially penetrating the skin, for example, the stratum corneum, upon application of a force to the electrode. Penetration of the skin reduces skin impedance and the potential to produce motion artifacts, thereby increasing the signal quality received by the electrode.

The invention is a skin preparation and monitoring electrode for application to a patient's skin to receive biopotentials conducted by the skin. The skin preparation and monitoring electrode has an electrode body including a support structure moveable from a first position to a second position upon application of a force to the support structure. The support structure returns to its first position upon removal of the force from the support structure. A skin penetration structure extends from the support structure such that the skin penetration structure penetrates the patient's skin when the support structure is in the second position and the skin penetration structure is withdrawn from the patient's skin when the support structure is in the first position.

In accordance with further aspects of the invention, the electrode is conformable to the contours of a patient's skin and is attached to the skin by an adhesive. The skin penetration structure comprises a plurality of tines integrally formed into a resiliently deformable support structure. The tines penetrate the stratum corneum when the electrode is in the second position and are withdrawn when the electrode returns to the first position. Removal of the tines from the skin before receiving biopotentials prevents the possibility of skin laceration due to electrode movement with respect to the skin.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 3 is a vertical cross section of the skin preparation electrode of FIG. 1 as it appears when first placed on the skin.

FIG. 4 is a vertical cross section of the skin preparation electrode of FIG. 1 as it appears after application of a force to the electrode.

DETAILED DESCRIPTION OF THE PREFERRED EMBODIMENT

Figure 1:
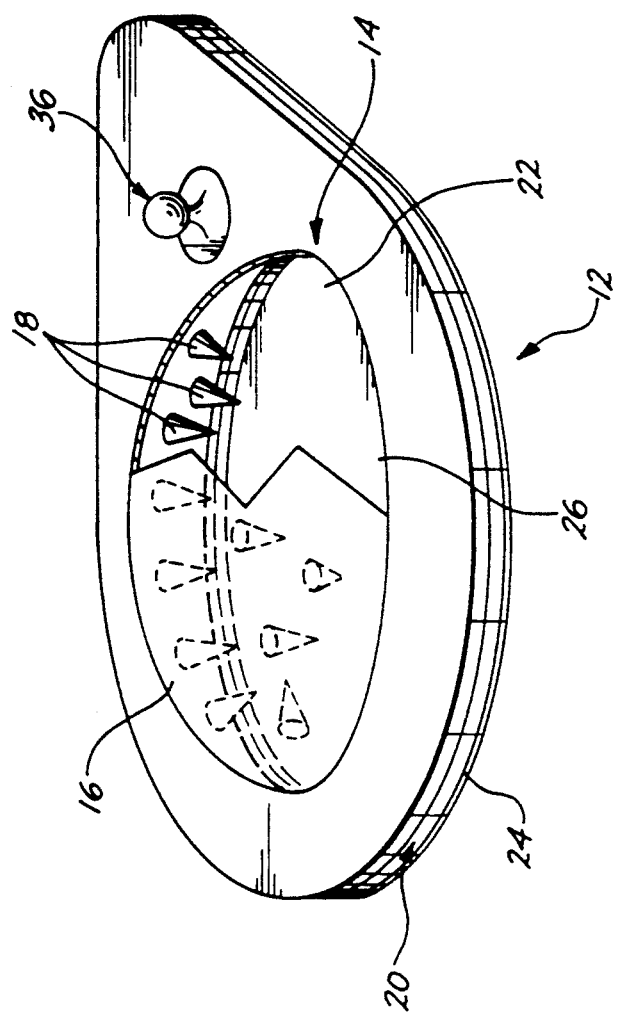
FIG. 1 is a perspective view of a first exemplary embodiment of a skin preparation electrode in accordance with the invention.

The combined skin preparation and monitoring electrode of the present invention allows one to prepare a patient's skin and attach a monitoring electrode for receiving biopotentials without expensive equipment or labor intensive preparation. Skin impedance and the propensity of the skin to generate motion artifacts when disturbed are reduced by piercing the patient's skin using a skin penetration structure built into a disposable electrode.

FIGS. 1-4 illustrate a first exemplary embodiment of a skin preparation and monitoring electrode 12 in accordance with the invention. Electrode 12 includes an electrode body 14, a resilient dome 16, a plurality of penetration tines 18 that project from the inner surface of the dome, an adhesive support structure 20, a conductive pad 22 saturated with electrolyte gel, and a release liner 24. The electrode body 14 provides support for the dome 16. The adhesive support structure 20 is coupled between the electrode body 14 and release liner 24. The electrode body 14 provides a cavity 26 that houses the conductive pad 22. To attach the electrode, the release liner 24 is removed and the electrode positioned on the skin 30 of a patient, as shown in FIG. 3.

Electrode 12 also includes an eyelet 34 and stud 36 combination that is coupled to the conductive pad 22. A snap connector 38 releasably connects the eyelet/stud combination to a conductor 40, which in turn is coupled to medical and diagnostic equipment (not shown). Thus, a conductive path is formed between the electrolyte gel in the conductive pad 22 and the medical and diagnostic equipment.

The electrode body 14 is preferably formed of a material that conforms to the patient's body and is tailored to have a desired degree of resiliency. A suitable material for the electrode body 14 is polyurethane on the order of 1 millimeter (mm) thick.

The resilient dome 16 is movable from a first position where the penetration tines 18 are not in contact with the skin 30 (FIG. 3), to a second position where the penetration tines 18 pierce the patient's skin (FIG. 4). The resilient dome 16 is deformed by applying force in the direction of the patient's skin, for example, using a finger 42. This method of skin preparation is performed after the electrode 12 is applied but prior to the acquisition of biopotentials. Upon removal of the force, the resilient nature of the dome 16 causes the dome to return substantially to its first position, shown in FIG. 3. This results in the penetration tines 18 being withdrawn from the patient's skin.

The surface area of the dome 16 is preferably not much larger than the surface area of a finger tip. The height of the dome 16 is dependent on the nature of the penetration tines 18, as well as the thickness of conductive pad 22 and support structure 20. The height of the dome is such that the penetration tines are fully withdrawn from the skin after pressure is released from the dome 16, illustrated in FIG. 3. The thickness of the conductive pad 22 and support structure 20 is preferably 3.5 mm, and the penetration tines 18 are preferably 4 mm long. A suitable height for the dome is then on the order of 4 mm. Thus, the relationship of the length of the penetration tines 18 and thickness of the conductive pad 22 is such that tines penetrate through the conductive pad and into the skin 30 by approximately 0.5 mm. The amount of desired penetration generally is that required to pierce through the stratum corneum or horny layer of skin.

Penetration of the stratum corneum will reduce the effects of motion artifacts, i.e., variations in skin resistance that occur through compression or extension of the layers of skin surrounding the electrode. The force required to deform the dome 16 should be between 500 and 2000 grams, but preferably is on the order of 1000 grams. Some minimal force is required to prevent inadvertent activation of the device and a maximum force is based on user capability.

As is shown most clearly in FIG. 1, the penetration tines 18 (not shown to scale) extend from the inside or concave surface of dome 16 along a plurality of axes that are approximately normal to tangent lines extending along the outside or convex surface of the dome 16. The penetration tines 18 may, for example, be roughly conical projections of material formed by stamping or injection molding, and may be formed as either part of the dome 16 or formed separately and attached to the dome 16 later. Approximately fifteen penetration tines 18 are employed in the embodiments shown to effectively reduce skin impedance without significantly damaging the patient's skin. Each penetration tine 18 is preferably formed of rigid plastic, has a length on the order of 0.5 mm longer than the thickness of the gel pad (that required to effectively puncture the stratum corneum of the skin), and is sharp enough to penetrate the skin easily. In a realized embodiment, the penetration tines 18 taper to a 20 degree angle at the tip.

The support structure 20 provides an adhesive method of attaching electrode 12 to the patient's skin 30. Support structure 20 is typically a polyethylene foam pad coated on one side with an acrylic adhesive for attachment to the skin 30 of the patient, and secured adhesively on the other side to the perimeter of electrode body 14. When the electrode 12 is positioned on a body, an enclosure 44 is formed by the electrode body 14, dome 16, support structure 20, and skin 30 (shown in FIG. 3). The enclosure 44 contains the conductive pad 22 which is preferably formed of an open-celled foam saturated with an electrolyte gel. An alternative to using the conductive pad 22 is to use a solid gel that would retain its relative position within electrode 12 without the need for an open-celled foam support structure. As a third alternative, liquid gel may also be added within the enclosure. In the third alternative, the enclosure is preferably only partially filled with gel to enable dome 16 to be readily compressed, as liquids are generally incompressible. Alternatives to only partially filling the cavity with liquid electrolyte gel include using gas-filled saran micro-bubbles within the gel formulation, thereby providing at least some compressibility, or providing an alternate route for the gel to escape the enclosure 44 during compression of dome 16.

The electrolyte gel within the conductive pad 22 forms an ionically conductive bridge between the skin, the eyelet 34, and stud 36 transforming the ion flow of the biopotential to electron flow. The eyelet 34 is preferably of a silver/silver chloride compound and is held in place by the stud 36, which is crimped around the eyelet. A suitable material for the stud is a nickle-plated brass. The eyelet 34 and stud 36 are offset from the resilient dome 16 so that they do not interfere with movement of the dome.

Stud 36 is in electrical contact with eyelet 34 and forms a method of electrical attachment to connector 38. The connector includes a conductive receptacle that makes electrical contact with stud 36, thereby coupling the stud to medical and diagnostic equipment via conductor 40. Thus, an electrically conductive path extends from the medical equipment, through the eyelet 34, conductive pad 22, and finally to the patient's skin 30. As an alternative to the eyelet/stud combination, a one-piece eyelet or other means known in the art may be used to provide for attachment to conductor 40.

The release liner 24 is placed over the conductive pad 22 and the acrylic adhesive layer on the support structure 20 to protect these layers from contamination and drying out during shipment and storage of the electrode 12. The release liner 24 is removed from the electrode 12 just prior to placing an electrode on a patient.

As will be appreciated by those skilled in the art, the invention allows a practitioner to eliminate time consuming skin preparation methods that are often used to attach monitoring electrodes. Instead, the electrode 12 is simply positioned on the patient's skin and a force is applied to the electrode in the direction of the patient's skin. The applied force causes dome 16 to move from its first position (FIG. 3), where the tines are above the skin, to its second position (FIG. 4) where the tines puncture the skin. As a result, tines 18 penetrate the patient's skin 30. When the applied force is removed from dome 16, the tines 18 withdraw from the patient's skin, ensuring that the electrode 12 receives consistent biopotential signals and reducing the chance of cutting the skin should there be electrode movement.

In a second exemplary embodiment of the invention, the electrode 12 illustrated in FIGS. 1-4 is initially configured in the manner illustrated in FIG. 4, with the structural design of dome 16 changed to have the dome 16 initially inverted (concave in shape when looking at the top of the dome). The penetration tines 18 thus extend through the conductive pad 22 prior to application to the patient's skin 30. When the electrode 12 is initially removed from the release liner 24 and applied to the patient's skin 30, the penetration tines 18 engage and penetrate the skin. In contrast to the exemplary embodiment described above, force is applied to the outer periphery of the electrode 12 and not to the dome 16 itself. Thus, the finger 42 would not be positioned on top of the dome 16 as illustrated. Continued application of force necessary to affix the electrode to the patient's skin then causes the dome 16 to snap back and away from the skin, with the penetration tines 18 exiting out and away from the skin, to a configuration similar to that shown in FIG. 3. This alternate embodiment requires a relatively complex protective cover, for example, a thicker cover to protect the protruding tines from damage during shipment as compared to the first embodiment. More particularly, a cover must be formed to protect the penetration tines 18 and conductive pad 22. Otherwise, packaging and shipping could damage the electrode 12.

Figure 5:
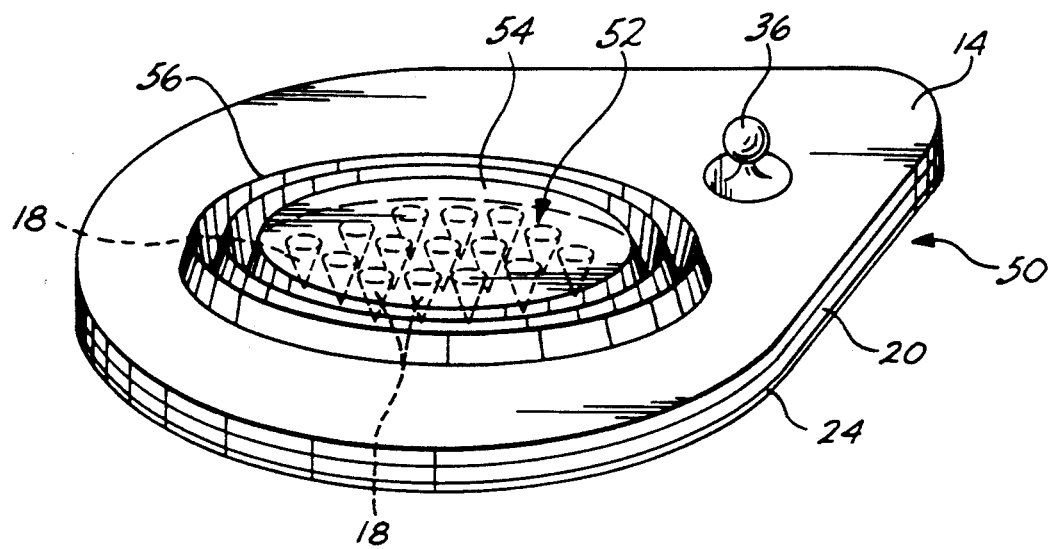
FIG. 5 is a perspective view of a third exemplary embodiment of a skin preparation electrode in accordance with the invention.
Figure 6:
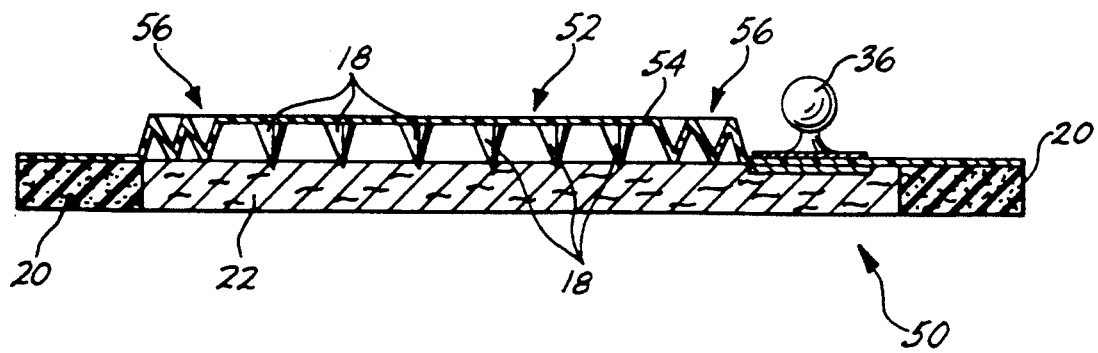
FIG. 6 is a vertical cross section of the skin preparation electrode of FIG. 5, showing more clearly the convoluted dome.

FIGS. 5 and 6 illustrate a third exemplary electrode 50 in accordance with the invention. The dome 16 of electrode 12 in FIGS. 1-4 is replaced with a diaphragm 52. The diaphragm includes a circular middle portion 54 and a convoluted or folded portion 56 that extends around the outer periphery of the middle portion 54, thereby providing resiliency to the diaphragm. The diaphragm can be formed by, for example, injection molding of plastic or via thermoforming techniques as applied to plastic sheet stock. Electrode 50 functions in an identical manner to electrode 12. Aside from the diaphragm 52, the structure of electrode 50 is generally the same as electrode 12 and similar elements are identically labeled.

The diaphragm 52 enables a more controlled and linear motion of the tines 18 as compared to the dome while still providing the same general degree of travel of the tines 18 into the skin and sufficient resiliency to return to the original configuration after application of force. The diaphragm is preferably comprised of a plastic material such as polyvinyl chloride approximately 0.2 to 0.5 mm thick.

Figure 7:
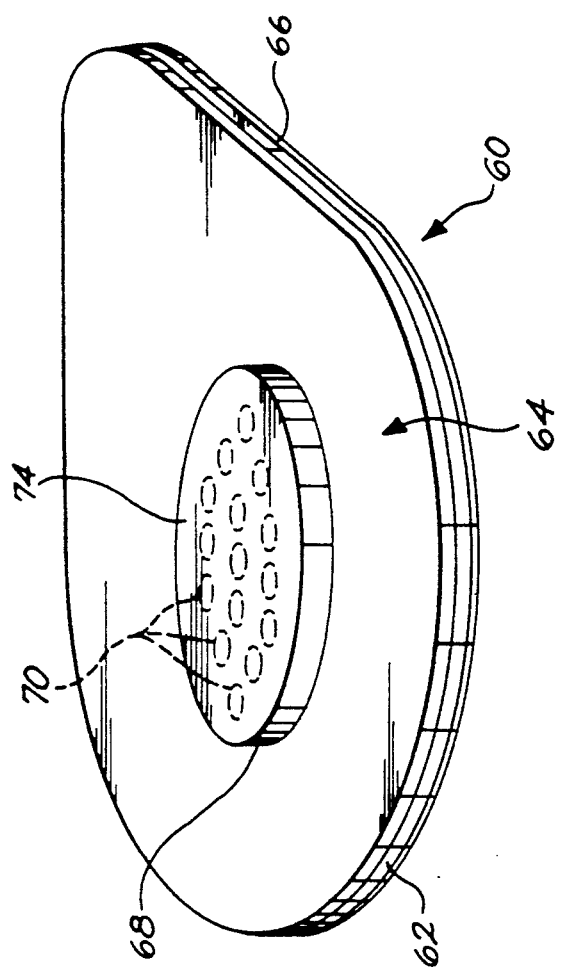
FIG. 7 is a perspective view of a fourth exemplary embodiment of a skin preparation electrode in accordance with the invention.
Figure 8:
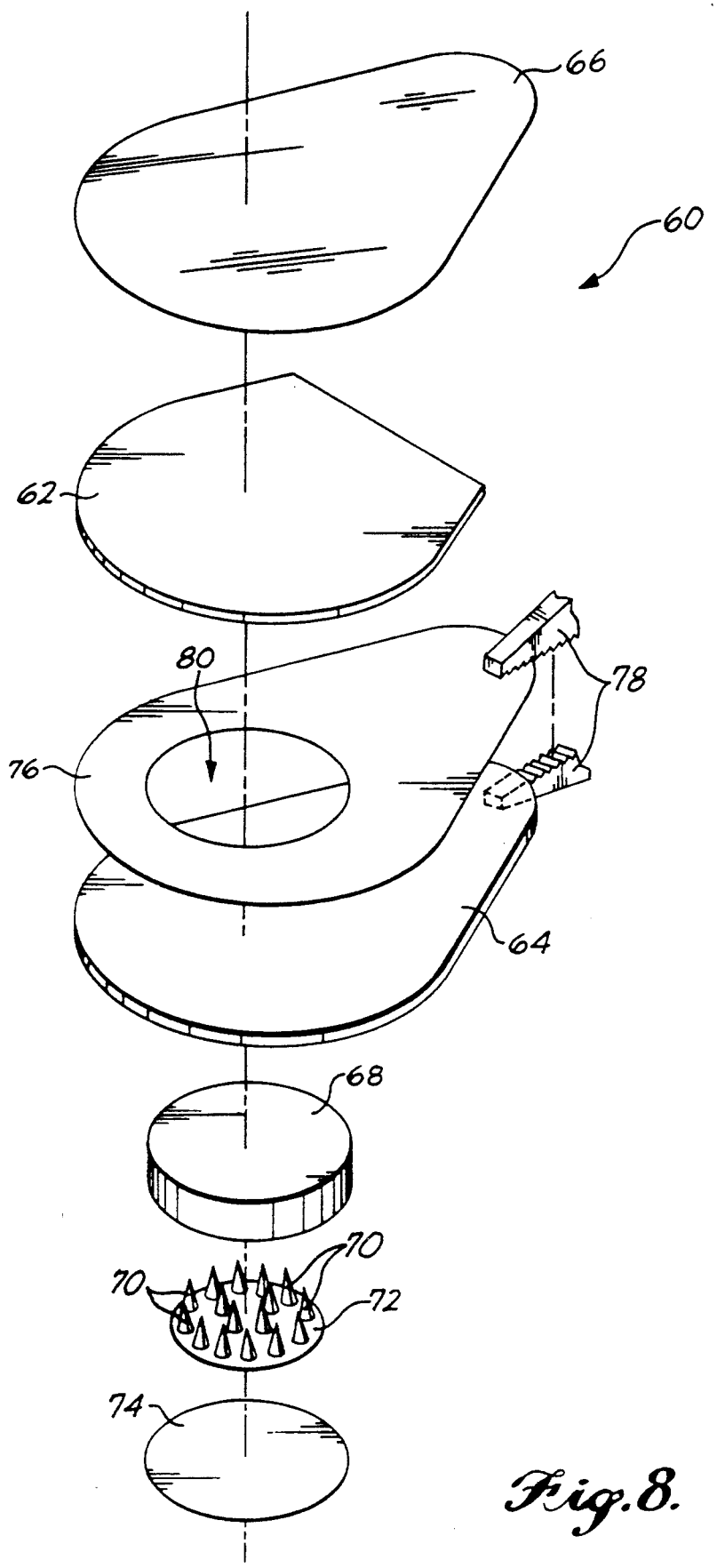
FIG. 8 is an exploded view of the skin preparation electrode of FIG. 7.

A fourth exemplary electrode 60 in accordance with the invention is illustrated in FIGS. 7 and 8. Electrode 60 utilizes a layer of solid conductive adhesive material 62 to both attach the electrode 60 to the patient's skin 30 and provide ionic conductivity, in effect replacing the conductive pad 22 and support structure 20 used in electrodes 12 and 50 of FIGS. 1-6. In addition to the solid conductive adhesive 62, the electrode 60 includes an electrode body 64, a release liner 66, a resiliently deformable pad 68, a plurality of penetration tines 70 formed on a disc 72, and a rigid backing layer 74.

The electrode body 64 is preferably formed of a 0.1 mm thick polyester. A layer 76 of conductive material is deposited onto a patient side of the electrode body 64, between the electrode body and conductive adhesive material 62. A portion of the electrode body 64 is not covered, shown as aperture 80 in the conductive layer 76. The aperture 80 is approximately the same diameter as the deformable pad 68.

The conductive layer 76 couples a patient's skin (not shown) to medical and diagnostic equipment through a cable and some type of releasable connector, such as an alligator clip 78. Suitable materials that may be used in forming conductive layer 76 include, for example, conductive carbon layers, tin/tin chloride foil layer, silver layers, or silver/silver chloride layers. Exemplary methods of forming conductive layer 76 include painting, electrodeposition, foil lamination, or vacuum deposition. In a realized embodiment, the conductive layer 76 is of silver/silver chloride deposited in the form of an ink with a thickness on the order of 0.012 mm.

The conductive adhesive layer 62 is adhesively secured to the electrode body 64 on the patient side of the electrode body, i.e., on top of conductive layer 76. The release liner 66 is positioned on the conductive adhesive layer 62, opposite the electrode body 64. The release liner 66 protects the conductive adhesive layer 62 from contamination during storage, prior to application to a patient's skin. The conductive adhesive material 62 is preferably on the order of 1 mm thick and is formed, for example, of a karaya gum based composition or a synthetic polymer based composition containing electrolytes. Irrespective of the material used, the conductive adhesive layer provides an ionic conductivity bridge between the skin of a patient and layer 76.

The penetration tines 70 and disc 72 are preferably formed by stamping and then forming a material such as stainless steel having a thickness around 0.1 mm. An alternate method to stamping would be to (1) chemically etch the part from a stainless steel sheet and then (2) bend the tines to an angle of 90 degrees to the part to form the disc 72. The tines 70 are preferably 2 mm long, and taper to a 20 degree angle at the end thereof. In this embodiment, the tines 70 must protrude through the electrode body 64 and conductive adhesive layer 62 prior to contacting the skin. Although an alternate embodiment is contemplated wherein the electrode body 64 includes an aperture that corresponds to the aperture 80 in the conductive layer 76, the preferred embodiment helps to protect the tines 70 from salt contact and subsequent corrosion during shipment of the electrode 60. The tines 70 may also be formed by stamping a circular-shaped plastic material. As will be appreciated, if the tines 70 are formed of plastic, corrosion is not a problem and the electrode body 64 would then preferably include an aperture similar to aperture 80 of conductive layer 76.

The deformable pad 68 is preferably composed of polyethylene foam on the order of 3 mm thick, with the side that contacts the electrode body 64 being coated with an acrylic adhesive. As is shown most clearly in FIG. 8, the deformable pad 68 is held in place on the electrode body 64 by a layer of acrylic adhesive. The material used for foam pad should be compressible to just under one sixth its thickness, for example, around 0.5 mm, with a force between 500 and 2000 grams, preferably on the order of 1000 grams.

The electrode 60 is applied by first removing release liner 66 and applying the conductive adhesive layer 62 directly to a patient's skin. As is shown in FIG. 8, the alligator clip 78 or similar device is attached to the conductive layer 76 of the electrode body 64, at a point where the electrode body 64 is not covered with the conductive adhesive material 62. To prep a patient's skin, force is applied to backing layer 74 in a direction toward the skin. The applied force compresses the deformable pad 68, penetrating the penetration tines 70 through the electrode body 64, conductive adhesive layer 62, and finally into the skin of a patient. Upon removal of the applied force, the deformable pad 68 resiliently rebounds to substantially its original shape, thereby withdrawing the penetration tines 70 from the skin and at least partially back up through the gel pad 62. It is noted that the conductive layer 76 is not deposited in the area in which the tines 70 protrude through the electrode body 64. This is to avoid the potential of conductive material from being dragged into the skin by the tines.

Figure 2:
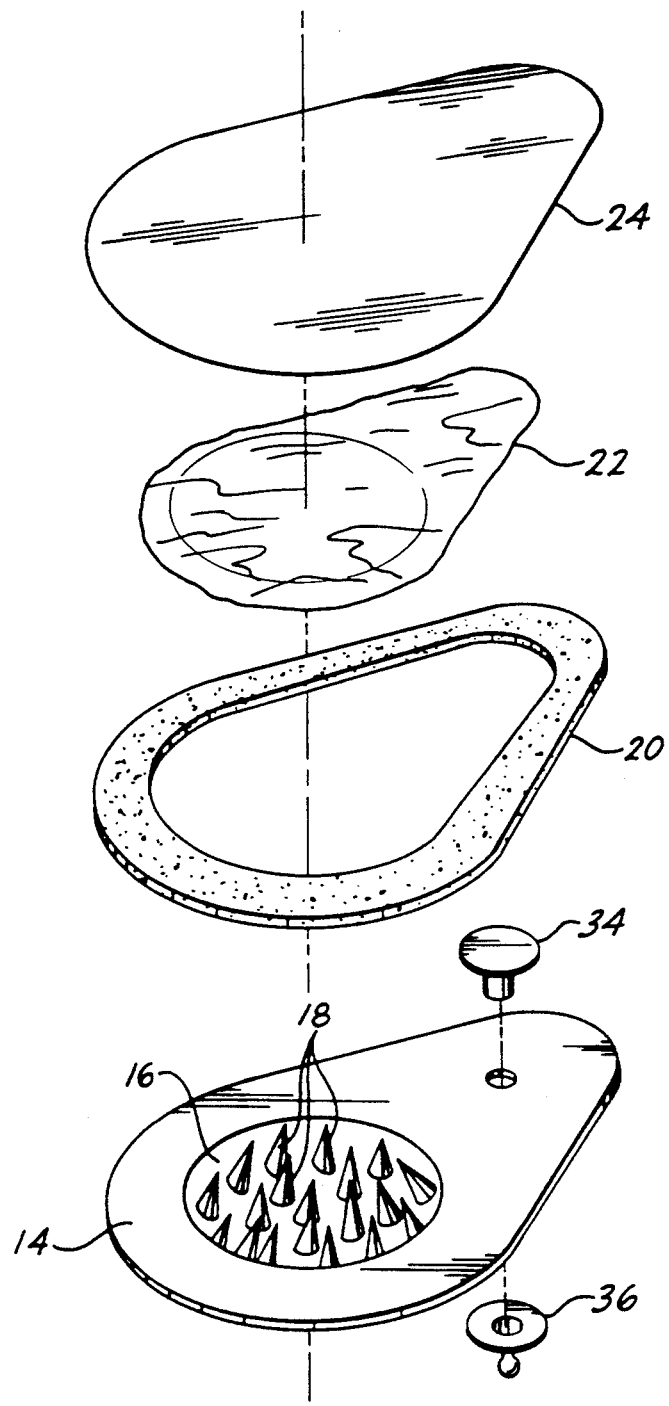
FIG. 2 is an exploded view of the skin preparation electrode of FIG. 1.

The electrode 60 of the invention is generally easier to construct, for example, using high speed automation equipment, than, for example, the stud 36 and eyelet 34 construction with the electrolyte-saturated conductive pad 22 of FIGS. 1 and 2, because the geometry of electrode 60 is less complex.

Although the invention has been illustrated and described in terms of preferred embodiments, it should be understood that other variations will be apparent to those skilled in the art. For example, it may be desirable to use tines shaped differently, made of different materials, or formed using different processes. It may also be desirable to change the configuration of the resilient dome to a different structure. Accordingly, the invention is not to be limited to the specific embodiments illustrated and described, the true scope and spirit of the invention are to be determined by the claims.

The embodiments of the invention in which an exclusive property or privilege is claimed are defined as follows:

1. A skin preparation and monitoring electrode for application to a patient's skin to receive biopotentials conducted by the skin, the electrode comprising:
   (a) an electrode body including support means for moving from a first position to a second position upon application of a force to the support means and for returning to the first position upon removal of the force from the support means;
   (b) conductive means, attached to the electrode body, for receiving biopotentials; and
   (c) skin penetration means, attached to the support means, for penetrating the patient's skin when the support means moves from the first position to the second position and withdrawing from the patient's skin when the support means moves from the second position to the first position.

2. The electrode of claim 1, wherein the electrode body is conformable to the patient's skin.

3. The electrode of claim 1, wherein the support means comprises a deformable resilient structure.

4. The electrode of claim 3, wherein the deformable resilient structure comprises a dome including a concave side and a convex side, and wherein the penetration means extend from the concave side when the support means is in the first position.

5. The electrode of claim 3, wherein the deformable resilient structure comprises a diaphragm having a top surface and a bottom surface, and wherein the penetration means extend from the bottom surface of the diaphragm structure.

6. The electrode of claim 3, wherein the deformable resilient structure comprises a compressible foam pad.

7. The electrode of claim 6, wherein the skin penetration means includes a plurality of tines and a circular base having a lower surface, the tines extending from the lower surface of the base.

8. The electrode of claim 1, wherein the skin penetration means comprises at least one tine.

9. The electrode of claim 1, further comprising attachment means for releasably attaching the electrode body to the patient's skin.

10. The electrode of claim 9, wherein the attachment means comprises a layer of adhesive material coupled to the electrode body.

11. A method of preparing a patient's skin to allow biopotentials conducted by the skin to be monitored, the method comprising the steps of:
   (a) positioning a monitoring electrode onto the patient's skin, the monitoring electrode including means for receiving biopotentials and penetration means for penetrating the patient's skin;
   (b) applying a force to the monitoring electrode in the direction of the patient's skin, to cause the penetration means to penetrate the patient's skin;
   (c) removing the force from the monitoring electrode, to allow the penetration means to withdraw from the patient's skin.

12. The method of claim 11, and further including the step of conforming the monitoring electrode to the contours of the patient's skin.

13. The method of claim 11, wherein the monitoring electrode includes a resiliently deformable structure and the steps of applying and removing force comprise applying and removing force to the structure.

14. The method of claim 11, further comprising the step of releasably attaching the monitoring electrode to the patient's skin with an adhesive.

15. A skin preparation and monitoring electrode for application to a patient's skin to receive biopotentials conducted by the skin, the electrode comprising:
   (a) an electrode body including support means for moving from a first position to a second position upon application of a force to the electrode body;
   (b) conductive means, attached to the electrode body, for receiving biopotentials; and
   (c) skin penetration means, attached to the support means, for penetrating the patient's skin when the support means is in the first position and for withdrawing from the patient's skin when the support means moves from the first position to the second position.

16. The electrode of claim 15, wherein the electrode body is conformable to the patient's skin.

17. The electrode of claim 15, wherein the support means comprises a deformable resilient structure.

18. The electrode of claim 17, wherein the deformable resilient structure comprises a dome including a concave side and a convex side, and wherein the penetration means extend from the convex side when the support means is in the first position.

19. The electrode of claim 15, wherein the skin penetration means comprises at least one tine.

20. The electrode of claim 15, wherein the electrode body includes an outer surface that extends around the periphery of the support means and wherein the application of force is applied to the outer surface of the electrode body.

* * * * *